United States Patent [19]

Böhme

[11] 4,229,575
[45] Oct. 21, 1980

[54] 7-(2,3-DIHYDROBENZO-5-FURANYL)-ACETAMIDO CEPHALOSPORIN DERIVATIVES

[75] Inventor: Ekkehard H. Böhme, Cincinnati, Ohio

[73] Assignee: Richardson-Merrell Inc., Wilton, Conn.

[21] Appl. No.: 881,611

[22] Filed: Feb. 27, 1978

[51] Int. Cl.$^2$ .......................................... C07D 501/56
[52] U.S. Cl. .................................... 544/27; 424/246; 544/21; 544/28
[58] Field of Search ........................... 544/28, 21, 27

[56] References Cited

U.S. PATENT DOCUMENTS

| 3,989,694 | 11/1976 | Berges | 544/27 |
| 4,000,133 | 12/1976 | Kariyone et al. | 544/27 |
| 4,020,060 | 4/1977 | Erickson et al. | 424/246 |
| 4,033,956 | 7/1977 | Erickson et al. | 424/246 |

Primary Examiner—Paul M. Coughlan, Jr.
Attorney, Agent, or Firm—William J. Stein; L. Ruth Hattan; George W. Rauchfuss, Jr.

[57] ABSTRACT

This invention is directed to new 7-(2,3-dihydrobenzo-5-furanyl)acetamido cephalosporin derivatives and methods for preparing them.

11 Claims, No Drawings

7-(2,3-DIHYDROBENZO-5-FURANYL)-ACETAMIDO CEPHALOSPORIN DERIVATIVES

BACKGROUND OF THE INVENTION

Field of Invention

This invention is directed to new cephalosporin derivatives which are useful as antibiotics and methods of preparing same.

SUMMARY OF THE INVENTION

Compounds of the formula 1 are useful as antibiotics

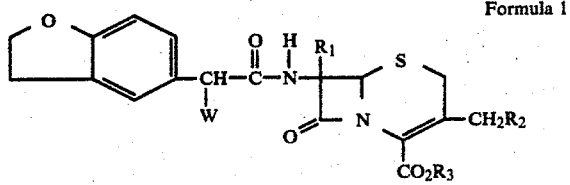

Formula 1 wherein W is H, $-NHR_4$, $-OH$, $-CO_2R_5$ or $-SO_3R_5$ wherein $R_4$ is hydrogen, a straight or branched 2 to 5 carbon alkanoyl group or an alkoxycarbonyl group in which the alkoxy moiety is straight or branched and has from 1 to 4 carbon atoms. $R_5$ is hydrogen or a straight or branched alkyl group of from 1 to 4 carbon atoms. $R_1$ is hydrogen or methoxy. $R_2$ is hydrogen, an alkanoyloxy group in which the alkanoyl moiety is straight or branched and has from 2 to 5 carbon atoms, or a heterocyclic thio group selected from 1,3,4-thiadiazol-2-ylthio, 5-methyl-1,3,4-thiadiazol-2-ylthio, 1,3,4-oxadiazol-2-ylthio, 5-methyl-1,3,4-oxadiazol-2-ylthio, tetrazol-5-ylthio, 1-methyltetrazol-5-ylthio, 1,2,3-triazol-5-ylthio and 1-methyl-1,2,3-triazol-5-ylthio. $R_3$ is hydrogen, a straight or branched alkyl group of from 1 to 4 carbon atoms, an alkanoyloxymethyl group in which the alkanoyl moiety is straight or branched and has from 2 to 5 carbon atoms, an alkanoylaminomethyl group wherein the alkanoyl moiety is straight or branched and has from 2 to 5 carbon atoms and the amino nitrogen may be substituted with a straight or branched alkyl group of from 1 to 4 carbon atoms, an alkoxycarbonylaminomethyl group wherein the alkoxy moiety is straight or branched and has from 1 to 4 carbon atoms and the amino nitrogen may be substituted with a straight or branched alkyl group of from 1 to 4 carbom atoms, a p-(alkanoyloxy)benzyl group in which the alkanoyl moiety has from 2 to 5 carbon atoms and is straight or branched, or an aminoalkanoyloxymethyl group wherein the alkanoyl moiety is straight or branched and contains from 2 to 15 carbon atoms and the amino nitrogen may be mono- or disubstituted with a straight or branched alkyl group of from 1 to 4 carbon atoms; and non-toxic pharmaceutically acceptable salts thereof.

DETAILED DESCRIPTION OF THE INVENTION

In formula 1, $R_3$ is hydrogen or a straight or branched alkyl group of from 1 to 4 carbon atoms. Or $R_3$ may be an alkanoyloxymethyl group represented by the formula

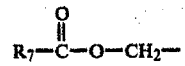

wherein $R_7$ is a straight or branched alkyl group of from 1 4 4 carbon atoms. Additionally, $R_3$ may be an alkanoylaminomethyl group or alkoxycarbonylaminomethyl group represented by

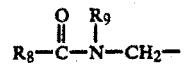

wherein $R_8$ is a straight or branched alkyl group of from 1 to 4 carbon atoms or a straight or branched alkoxy group of from 1 to 4 carbon atoms and $R_9$ is hydrogen or a straight or branched alkyl group of from 1 to 4 carbon atoms. $R_3$ may also be an alkanoyloxybenzyl group represented by the formula

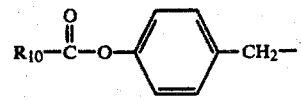

wherein $R_{10}$ is a straight or branched alkyl group of from 1 to 4 carbon atoms. $R_3$ may also be an aminoalkanoyloxymethyl group represented by the formula

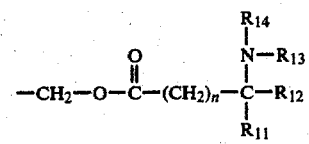

wherein n is 0 to 5, and each of $R_{11}$ and $R_{12}$ is selected from hydrogen or a straight or branched alkyl group of from 1 to 4 carbon atoms and each of $R_{13}$ and $R_{14}$ is selected from hydrogen or a straight or branched alkyl group of from 1 to 4 carbon atoms.

Illustrative examples of the straight or branched alkyl groups of from 1 to 4 carbon atoms which $R_3$ and $R_7$ to $R_{14}$, inclusive, may represent are: methyl, ethyl, n-propyl, isopropyl, n-butyl, isobutyl and tert-butyl.

Illustrative examples of the straight or branched alkoxy groups of from 1 to 4 carbon atoms which $R_8$ may represent are: methoxy, ethoxy, n-propoxy, isopropoxy, n-butoxy, sec-butoxy and tert-butoxy.

In formula 1, the substituent group $R_1$ is hydrogen or methoxy.

Additionally, in formula 1, $R_2$ is hydrogen, an alkanoyloxy group in which the alkanoyl moiety is straight or branched and has from 2 to 5 carbon atoms; or a heterocyclic thio group selected from 1,3,4-thiadiazol-2-ylthio, 5-methyl-1,3,4-thiadiazol-2-ylthio, 1,3,4-oxadiazol-2-ylthio, 5-methyl-1,3,4-oxadiazol-2-ylthio, tetrazol-5-ylthio, 1-methyltetrazol-5-ylthio, 1,2,3-triazol-5-ylthio, 1-methyl-1,2,3-triazol-5-ylthio and represented by the following respective structures:

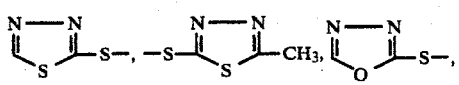

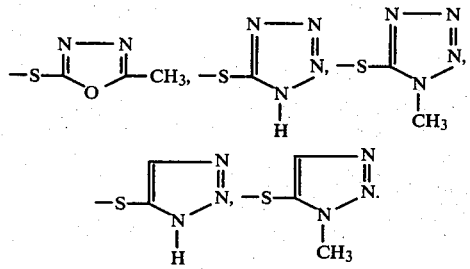

Illustrative examples of the alkanoyl groups represented by $R_2$ are the following: acetyl, propionyl and butyryl.

In the formula 1, W is hydrogen or hydroxyl. W is also —$NHR_4$ wherein $R_4$ is hydrogen, a straight or branched 2 to 5 carbon alkanoyl group or an alkoxycarbonyl group in which the alkoxy moiety is straight or branched and has from 1 to 4 carbon atoms.

Additionally, W is a —$COOR_5$ or an —$SO_3R_5$ group wherein $R_5$ is hydrogen or a straight or branched alkyl group of from 1 to 4 carbon atoms.

Illustrative examples of alkyl groups as represented by $R_5$ are: methyl, ethyl, n-propyl, isopropyl, n-butyl and tert-butyl.

Illustrative examples of the alkoxy groups of the alkoxycarbonyl groups represented by $R_4$ are: methoxy, ethoxy, n-propoxy, isopropoxy, n-butoxy and tert-butoxy.

Illustrative examples of the alkanoyl groups as represented by $R_4$ are acetyl, propionyl and isobutyryl.

It is apparent that $R_1$ exhibits either a cis or a trans spatial relationship with the hydrogen at position 6 in formula 1. The cis and trans isomers are within the scope of the invention; the compounds with the cis configuration being preferred.

The optical isomers of the compounds represented by formula 1 are also within the scope of this invention.

The non-toxic pharmaceutically acceptable acid addition salts of compounds of formula 1 such as mineral acids, for example, hydrogen chloride, hydrogen bromide, hydrogen iodide, sulfate, sulfonate and phosphate and organic acid addition salts, for example, maleate, acetate, citrate, oxalate, succinate, benzoate, tartrate, fumarate, malate, mandelate and ascorbate are also included within the scope of this invention.

Also within the scope of this invention are the non-toxic pharmaceutically acceptable salts of compounds of formula 1 wherein W represents —$CO_2R_5$ or —$SO_3R_5$ ($R_5$=H) and $R_3$ is hydrogen. Illustrative examples of these salts are the acid derivatives of primary, secondary and tertiary amines such as cyclohexylamine, dibutylamine, trioctylamine, procaine and dibenzylamine and the alkali metal and alkaline earth metal such as sodium, potassium, magnesium and calcium.

The compounds of this invention may be administered in a manner similar to that of many well known cephalosporin compounds, for example, cephalexin, cephalothin or cephaloglycine. They may be administered orally, parenterally or topically to warm blooded animals, that is, birds and mammals, for example, cats, dogs, cows, sheep, horses and humans. For oral administration the compounds may be administered in the form of tablets, capsules, or pills or in the form of elixirs or suspensions. For parenteral administration they may be used in the form of a sterile aqueous solution which may contain other solutes, for example, enough saline or glucose to make the solutions isotonic. For topical administration the compounds may be incorporated in creams, ointments, foams or sprays.

Illustrative examples of bacteria against which the compounds of this invention are active are Staphylococcus aureus, Streptococcus pyogenes, Escherichia coli and Klebsiella pneumonia.

An illustrative example of a compound of this invention is 7-[[amino(2,3-dihydro-5-benzofuranyl)acetyl-]amino]-3-methyl-8-oxo-5-thia-1-azabicyclo[4.2.0]oct-2-ene-2-carboxylic acid.

Compounds of formula 1 are prepared by coupling a compound of formula 2

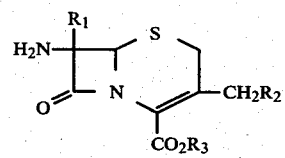

Formula 2 with a compound of formula 3

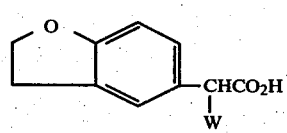

Formula 3 and functional equivalents thereof wherein $R_1$, $R_2$, $R_3$ and W have the meanings defined for formula 1. It is provided that when W is a reactive group such as —$NHR_4$ or —OH wherein $R_4$ is H, then these groups must be protected during the coupling reaction. It is further provided that when W is —$CO_2R_5$ or —$SO_3R_5$ wherein $R_5$ is hydrogen, then these groups may be protected during the coupling reaction. ("Cephalosporins and Pencillins," E. H. Flynn, Editor. Academic Press, Inc., N.Y. 1972 p. 88–90; J. Med. Chem., 9, 746 (1966); U.S. Pat. No. 3,286,926.) Optionally, N-ethoxycarbonyl-2-ethoxy-1,2-dihydroquinoline (EEDQ) may be used as a coupling agent in this reaction provided that when W is an —$NHR_4$, an —OH, a —$CO_2R_5$ or an —$SO_3R_5$ group, $R_4$ and $R_5$ being hydrogen, in compounds represented by formula 3, then these groups must be protected; and further, in compounds represented by formula 2; $R_3$ must be other than hydrogen. A dehydrating agent such as a carbodiimide may be used. The protecting group(s) may be removed during work up of the reaction mixture by adjusting the pH to 1.5 to 3 or wherein $R_3$, $R_4$ and/or $R_5$ are other than hydrogen by treating compounds of formula 1 with a 2 to 20 mole excess of an acid, e.g., trifluoroacetic acid at 0° to 30° C. for from 10 to 60 minutes.

Illustrative examples of protecting groups which are used for the specific reactive groups such as —$NHR_4$, —OH, —$CO_2R_5$ and —$SO_3R_5$ wherein $R_4$ and $R_5$ are H are as follows. For an amine group the protecting group may be an acid salt such as the hydrochloride or the hydrobromide, an alkoxycarbonyl group, for example, tert-butoxycarbonyl; or an alkanoyl group, for example, an acetyl group or a [3-ethoxy-1-methyl-3-oxo-1-propen-1-yl] group. The hydroxyl group may be protected with, for example, a trimethylsilyl group. Acid groups such as —$CO_2H$ or —$SO_3H$ may be protected with an alkyl group such as methyl, ethyl, tert-butyl or with an alkanoyloxymethyl group such as pivaloyloxymethyl. Compounds of formula 3 wherein W is a —NHR$_4$, —OH, —CO$_2$R$_5$ or an —SO$_3$R$_5$ group wherein R$_4$ and R$_5$ are hydrogen and said groups are protected may be prepared by methods described in the literature or by methods described herein.

The amine group of the amino acid compounds of formula 3, W is —NHR$_4$ (R$_4$ is hydrogen) may be protected by reaction with an alkanoyl halide of from 2 to 5 carbons in a solvent such as ethyl ether, tetrahydrofuran, methylene chloride, chloroform or benzene optionally in the presence of a base at from 0° to 50° C. for from 1 hour to 24 hours. Likewise, the amine group in the amino acid of a compound of formula 3 may be protected by reaction with an alkoxycarbonylazide, in a solvent such as ethyl ether, chloroform, tetrahydrofuran, methylene chloride or benzene optionally in the presence of a base at from 0° C. to about 50° C. for from 1 hour to 24 hours. The amine group of the amino acid of formula 3, W is —NHR$_4$ and R$_4$ is hydrogen, may be protected by reaction with the methyl, ethyl or propyl ester of acetoacetic acid. The reaction is conducted in a low molecular weight alcohol, that is, methanol, ethanol, propanol containing sodium or potassium hydroxide at reflux temperature for from 5 to 30 minutes to form an amine protected with a [3-ethoxy-1-methyl-3-oxo-1-propen-1-yl] group.

Compounds of formula 3 wherein W is —OH are protected by reacting said compounds with 1 equivalent of bistrimethylsilylacetamide in THF at reflux for 1 to 3 hours optionally in the presence of a basic material, for example, triethylamine.

The compounds of formula 3, W is —CO$_2$R$_5$ and R$_5$ is hydrogen, are protected by reacting 1 equivalent of the compound with 1 equivalent of thionyl chloride in a solvent such as ethyl ether, methylene chloride or benzene at from 10° C. to the boiling point of the solution for from 0.5 hour to 6 hours. The monoacid chloride is then reacted with a 1 to 4 carbon aliphatic alcohol optionally in the presence of an acid acceptor such as sodium bicarbonate or triethylamine at 10° to 80° C. for from 0.5 to 6 hours.

The compounds of formula 3, W is —SO$_3$R$_5$ and R$_5$ is hydrogen, are protected by reacting 1 equivalent of the compound with 2 to 3 equivalents of thionyl chloride in a solvent such as ethyl ether, methylene chloride, chloroform, carbon tetrachloride or benzene at from 20° C. to the boiling point of the solution for from 0.5 to 6 hours. The dichloride is isolated and reacted with 1 equivalent of water in ethyl ether at 10° to 30° C. for from 0.5 to 4 hours to hydrolyze the carboxylic acid chloride. The chlorosulfonyl acetic acid derivative thus formed is reacted with a 1 to 4 carbon aliphatic alcohol in an excess of the alcohol at from 10° to 80° C. optionally in the presence of an acid acceptor for from 0.5 to 6 hours to give the desired compound of formula 3 wherein W is —SO$_3$R$_5$ and R$_5$ is a 1 to 4 carbon alkyl group.

Functional equivalents of the acid as represented by compounds of formula 3 include the acid halide such as the acid chloride, acid anhydrides, including mixed anhydrides, with for example, alkylphosphoric acids, lower aliphatic monoesters of carbonic acid or alkyl or aryl sulfonic acids.

The coupling reaction is generally carried out in the presence of a solvent. Suitable solvents include ethyl acetate, chloroform, acetone, dioxane, tetrahydrofuran (THF), dimethylformamide (DMF), ether, ethanol, benzene and ethanol-benzene. As hydrophilic solvents are employed, mixtures of these solvents with water are also suitable for the above reactions. The coupling reaction is generally carried out in the presence of a base, for example, triethylamine or an alkaline bicarbonate. The temperature of the reaction may vary from −10° C. to 100° C., and the reaction time may vary from about 0.5 hour to 24 hours. The cephalosporin products are isolated by conventional means.

The acids as represented by compounds of formula 3 may be coupled as the (D), the (L) or mixtures of the (D) and (L) optical isomers when W is other than hydrogen or —CO$_2$R$_5$. When W is hydrogen or —CO$_2$R$_5$, no optical activity is present and these compounds are coupled as described above.

Illustratively, an acid as represented by formula 3 may be coupled to a compound as represented by formula 2 using the general procedure described in *J. Med. Chem.*, 9, 746 (1966) with the proviso that when W is other than hydrogen, these groups such as —NHR$_4$, —OH, —CO$_2$R$_5$ and —SO$_3$R$_5$, R$_4$=R$_5$=H, must be protected. The acid to be coupled is reacted with a slight excess (1.05 equivalents) of an alkylchloroformate such as isobutylchloroformate at about −10° C. in a solvent which contains an acid acceptor such as triethylamine or sodium bicarbonate. After reaction is complete, 1 equivalent of a compound represented by formula 2 is added, the temperature is raised from −10° C. to about 20° C. and the reaction completed after 2–3 hours. The coupled product is recovered by known means.

Illustratively, an acid, as represented by compounds of formula 3 wherein W is H, OH, —NHR$_4$, —CO$_2$R$_5$ and —SO$_3$R$_5$ (R$_4$=R$_5$=H) may be coupled to an amine as represented by a compound of formula 2 in a suitable solvent by the use of a carbodiimide, for example, N,N'-dicyclohexylcarbodiimide by the general procedure as taught in U.S. Pat. No. 3,252,973, with the proviso that when W is other than H and R$_4$=R$_5$=H, then the groups represented by W may be protected.

Illustratively, an acid as represented by a compound of formula 3 may be coupled to an amine as represented by a compound of formula 2 utilizing EEDQ according to the general procedure found in *J. Am. Chem. Soc.*, 90, 1651 (1968) with the proviso that active groups such as —NHR$_4$, —OH, —CO$_2$R$_5$ or —SO$_3$R$_5$ (R$_4$=R$_5$=H) as represented by W must be protected and a further proviso that R$_3$ is other than hydrogen. Equivalent amounts of an acid, as represented by formula 3, and an amine, as represented by formula 2, and EEDQ in a suitable solvent such as benzene, chloroform, ethanol or THF at a temperature of from 10° C. to about 80° C. are reacted for about 1 to 24 hours. The solvent is removed and the coupled product is recovered by conventional methods.

Illustratively, an acid as represented by a compound of formula 3 may be converted to an acid chloride by means well-known in the art. The active groups such as —NHR$_4$, —OH, where R$_4$ is hydrogen are protected and groups such as —CO$_2$R$_5$ or —SO$_3$R$_5$, R$_5$=H, may be protected prior to formation of acid chloride. The acid chloride is reacted with an amine as represented by formula 2 in a suitable solvent which generally contains an acid acceptor such as triethylamine or an alkaline bicarbonate at a temperature of from 10° to 100° C. for from 0.5 hour to 4 hours. The cephalosporin derivative is recovered by conventional means.

Compounds of formula 2 wherein R$_1$ is hydrogen, R$_2$ is hydrogen or acetyloxy and R$_3$ is hydrogen are commercially available or may be prepared by methods well known in the art. Compounds of formula 2 wherein $R_1$ is methoxy, $R_2$ is hydrogen or acetyloxy and $R_3$ is hydrogen are prepared according to the general procedures described in U.S. Pat. No. 3,778,432.

Compounds of formulas 1 and 2 wherein $R_3$ is alkanoyloxymethyl may be prepared by reacting the corresponding acid, $R_3$ is hydrogen, in the form of a salt, such as, an alkali metal salt (sodium) or the triethylammonium salt with an equivalent of a compound of the formula:

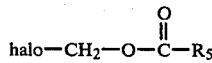

wherein halo is chlorine or bromine, and $R_5$ is a straight or branched alkyl group of from 1 to 4 carbon atoms, by the general procedure described in U.S. Pat. No. 3,655,658.

Compounds of formulas 1 and 2 wherein $R_3$ is alkanoylaminomethyl or alkoxycarbonylaminomethyl are prepared by treating an alkali metal salt such as the sodium salt of the corresponding acid, $R_3$=hydrogen, derivatives of formulas 1 and 2 in an organic solvent such as dimethylformamide or hexamethylphosphoramide at a temperature of 10° to 30° C. with an equivalent amount of an alkanoylaminomethyl halide or an alkoxycarbonylaminomethyl halide for ½ to 3 hours after which the mixture is poured into ice water. The resulting precipitated product is isolated by standard procedures.

Compounds of formulas 1 and 2 wherein $R_3$ is p-(alkanoyloxy)benzyl are prepared by adding two equivalents of the p-(alkanoyloxy)benzyl alcohol to an equivalent of the alkali metal salt such as the sodium salt of the corresponding acid derivative, $R_3$=hydrogen, of formulas 1 and 2 in dimethylformamide or hexamethylphosphoramide after which the mixture is cooled to 0° C. One to 2 equivalents of dicyclohexylcarbodiimide in dimethylformamide are added dropwise to the mixture with stirring. The mixture is stirred at 0° C. for ½ to 3 hours and then an additional 2 to 5 hours at 10° to 30° C. The formed dicyclohexylurea is removed by filtration. The filtrate is diluted with chloroform, methylene chloride or ethyl acetate, washed with water, dried and evaporated to give the product.

Compounds of formulas 1 and 2 wherein $R_3$ is aminoalkanoyloxymethyl are prepared by mixing a suspension of the alkali metal salt such as the sodium salt of the corresponding acid, $R_3$=hydrogen, of formulas 1 and 2 and an excess of an appropriate amine protected aminoalkanoyloxymethyl halide in a solvent such as dimethylformamide, hexamethylphosphoramide or dimethylsulfoxide for 2 to 96 hours at 10° to 30° C. The mixture is then diluted with a solvent such as ethyl acetate or methylene chloride, washed with water, aqueous base, then water. The organic phase is separated and the precipitate isolated by conventional means followed by deprotection of the amine group to give the product.

Compounds represented by formulas 1 and 2 wherein $R_1$ is hydrogen or methoxy, $R_2$ is a heterocyclic thio group as described in formula 1 and $R_3$ is hydrogen are prepared by dissolving 1 equivalent of an acid, represented by compounds of formula 1 or 2 wherein $R_1$ is hydrogen or methoxy, $R_2$ is acetyloxy, and $R_3$ is hydrogen, in the form of an alkali metal salt, such as the sodium salt, in about 500 to 2000 ml of water at a temperature of from about 30° to about 90° C. under a nitrogen atmosphere, and then adding 1 equivalent of a base, such as, sodium bicarbonate or triethylamine and 1 to 3 equivalents of the appropriate heterocyclic thiol selected from a compound having the following structure:

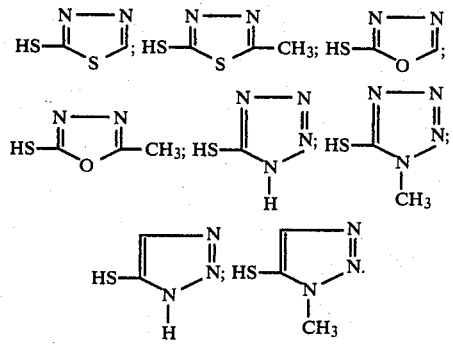

The solution is stirred from 2 to 6 hours at 30° C. to 90° C. and the product isolated by conventional means. The displacement of the acetyloxy group by the heterocyclic thiol compounds is also realized when compounds of formula 1, $R_1$ is hydrogen or methoxy, $R_2$ is acetyloxy, and $R_3$ is hydrogen, are treated with an appropriate heterocyclic thiol according to the general procedure described in J. Antibiotics, 23, 131 (1966).

The compound of formula 3 wherein W is an amine group is prepared by a modification of the method described in Tetrahedron, 31, 863 (1975).

For example, equivalent amounts of α-hydroxyhippuric acid and 2,3-dihydrobenzofuran in a suitable solvent such as 5% to 50% sulfuric acid-95% to 50% acetic acid mixture, or from 50% to 100% sulfuric acid are reacted at from 0° to about 25° C. for from 1 hour to 72 hours. α-Benzamido-(2,3-dihydro-5-benzofuranyl)acetic acid is recovered from the reaction mixture.

α-Amino(2,3-dihydro-5-benzofuranyl)acetic acid may be recovered from the corresponding α-benzamido derivative which is dissolved in a low molecular weight alcohol such as methanol, ethanol, isopropanol, butanol or water and subjected to hydrogen gas at a pressure of from 10 to 70 pounds/in² in the presence of a suitable catalyst such as palladium on carbon or palladium on barium sulfate for from 1 to 8 hours at a temperature of from 20° to 50° C. or by treating said α-benzamido derivative dissolved in a low molecular weight alcohol such as methanol, ethanol, isopropanol or butanol or water containing a suitable mineral acid such as sulfuric, hydrochloric, hydrobromic or phosphoric acid for from 1 to 8 hours at a temperature of from about 30° to 110° C. and treating the thus formed acid salt with a base such as triethylamine, sodium hydroxide, potassium bicarbonate, sodium bicarbonate or a basic ion exchange resin such as Amberlite IR45 ® to form α-amino(2,3-dihydro-5-benzofuranyl)acetic acid.

Compounds of formula 3 wherein W is —NHR$_4$ and R$_4$ is a 2 to 5 carbon alkanoyl group or an alkoxycarbonyl group wherein the alkoxy group contains 1 to 4 carbon atoms may be prepared by the following procedures. An amine compound represented by formula 3 wherein W is —NHR$_4$ and R$_4$ is hydrogen is reacted in a suitable solvent such as ethyl ether, tetrahydrofuran, methylene chloride, chloroform or benzene with a 2 to 5 carbon acid halide, wherein the halide is chlorine or bromine, for example, acetyl chloride, propionyl chloride or butyryl bromide at 0° to 50° C. for from 1 to 24 hours optionally in the presence of a basic material such as triethylamine, sodium bicarbonate or sodium carbonate to give a compound of formula 3 wherein $R_4$ is a 2 to 5 carbon alkanoyl group.

An amine compound represented by formula 3 wherein W is —$NHR_4$ and $R_4$ is hydrogen may be reacted with an alkoxycarbonylazide wherein the alkoxy group is from 1 to 4 carbon atoms, for example, ethoxycarbonylazide, propoxycarbonylazide or isobutoxycarbonylazide in a suitable solvent such as ethyl ether, tetrahydrofuran, methylene chloride, chloroform or benzene optionally in the presence of basic material such as triethylamine, sodium bicarbonate or sodium carbonate at a temperature of from 0° to 50° C. for from 1 to 24 hours to produce a compound of formula 3 wherein W is —$NHR_4$ and $R_4$ is a 1 to 4 carbon alkoxycarbonyl group.

The compound of formula 3 wherein W is a hydroxyl group may be prepared from the corresponding amine compound of formula 3, W is —$NHR_4$ and $R_4$ is hydrogen. One equivalent of α-amino(2,3-dihydro-5-benzofuranyl)acetic acid in a suitable acid such as hydrochloric, hydrobromic, sulfuric, phosphoric or acetic acid is reacted with 1 to 3 equivalents of an alkali metal nitrite such as sodium nitrite or potassium nitrite at a temperature of from 30° to 70° C. for from 2 to 8 hours to give the desired α-hydroxy(2,3-dihydro-5-benzofuranyl)acetic acid.

The compound of formula 3 wherein W is hydrogen is prepared from the thus produced α-hydroxyacetic acid derivative. The compound of formula 3 wherein W is hydroxyl is added to a low molecular weight alcohol such as methanol, ethanol, propanol or butanol which contains a suitable acid catalyst such as sulfuric, phosphoric, hydrochloric, or hydrobromic and is refluxed for from 1 to 6 hours and the α-hydroxy ester corresponding to the low molecular weight alcohol used is then recovered. The thus formed α-hydroxy ester may be reacted with either an acid anhydride such as acetic anhydride, propionic anhydride and butanoic anhydride or an alkanoyl halide such as acetyl chloride, propionyl bromide or butyryl chloride in a suitable solvent such as ethyl ether, tetrahydrofuran, methylene chloride or n-propyl ether at a temperature of from 10° C. to the reflux temperature of the solvent used for from 1 to 6 hours. The alkanoyloxy ester derivative recovered is added to a low molecular weight alcohol such as methanol, ethanol, propanol or butanol and is treated with hydrogen gas at a pressure of 20 to 60 pounds/$in^2$ at 10° to 30° C. for from 1 to 4 hours in the presence of a suitable catalyst such as palladium on carbon or palladium on barium sulfate. Basic hydrolysis of the ester with sodium hydroxide or potassium hydroxide followed by acid treatment gives a compound of formula 3 wherein W is hydrogen.

A compound represented by formula 3 wherein W is —$CO_2R_5$ and $R_5$ is hydrogen or a 1 to 4 carbon alkyl group may be prepared by reacting a corresponding compound wherein W is hydrogen with 2 to 3 equivalents of lithium diisopropylamide or lithium diisopropylamine in a suitable solvent such as ethyl ether, propyl ether or tetrahydrofuran at —50° to 50° C. for from 1 to 2 hours. The dianion thus formed is reacted with a suitable carboxylating agent such as methyl chloroformate, ethyl chloroformate, propyl chloroformate, butyl chloroformate, dimethylcarbonate or diethylcarbonate at —70° to —50° C. for from 10 to 60 minutes and recovering the monoester of a substituted malonic acid and hydrolyzing the ester with a suitable base such as sodium hydroxide or potassium hydroxide, followed by treatment with a suitable acid such as hydrochloric, sulfuric or phosphoric to give the substituted malonic acid.

A compound represented by formula 3 wherein W is —$SO_3R_5$ and $R_5$ is hydrogen or a 1 to 4 carbon alkyl group may be prepared by reacting the corresponding compound wherein W is hydrogen with 1 to 2 equivalents of the dioxane-sulfur trioxide reagent in a suitable solvent such as methylene chloride, chloroform, carbon tetrachloride, ethylene dichloride or tetrachloroethane at a temperature of 0° to 30° C. for from 10 to 18 hours wherein the α-sulfo-(2,3-dihydro-5-benzofuranyl)acetic acid is obtained. The thus obtained acid is treated with 2 to 3 equivalents of a suitable reagent such as, for example, the bromide or chloride, of phosphorus pentahalide, phosphorus trihalide, phosphorus oxyhalide or thionyl halide in a suitable solvent such as ethyl ether, methylene chloride, chloroform or carbon tetrachloride or benzene at from 20° C. to the boiling point of the solution for from 0.5 to 6 hours to form the diacid halide; reacting the thus formed diacid chloride with 1 equivalent of water at 10° to 30° C. for from 0.5 to 4 hours in a suitable solvent such as ethyl ether, methylene chloride, chloroform, carbon tetrachloride or benzene and reacting the thus formed chlorosulfonyl acetic acid derivative with a 1 to 4 carbon alcohol such as methanol, ethanol, propanol or butanol optionally in the presence of a solvent such as ethyl ether or methylene chloride and optionally in the presence of an acid acceptor such as triethylamine, sodium bicarbonate or potassium carbonate at 70° to 80° C. for from 0.5 hour to 6 hours to form the ester corresponding to the alcohol employed of the α-(alkoxysulfony)(2,3-dihydro-5-benzofuranyl)acetic acid.

The compounds of formula 3 wherein W is as defined in formula 1 and the optical isomers of compounds of formula 3 wherein W is —$NHR_4$, —OH, —$SO_3R_5$ wherein $R_4$ and $R_5$ are as defined in formula 1 are deemed part of this invention. The compounds of formula 3 defined above are useful in the synthesis of the cephalosporin derivatives of this invention. The cephalosporin derivatives are active as antibacterial agents.

The resolving agent used to separate the optically active isomers of α-amino(2,3-dihydro-5-benzofuranyl)acetic acid is binaphthylphosphoric acid (BPA), formula 4, the structure of which is shown below.

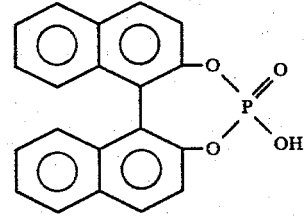

Formula 4

This material is fully described in *Tetrahedron Letters*, (1971), 4617. The acid used in this invention is (+)-BPA.

For the resolution, about 2 to 3 equivalents of the racemic mixture (D, L) of the compound of formula 3, W is —$NHR_4$ ($R_4$=H), 1 to 2 equivalents of (+)-BPA and 1 to 3 equivalents of hydrogen chloride in methanol are refluxed for 10 to 60 minutes. The salt formed between the (+)-BPA and (D)-α-amino(2,3-dihydro-5-benzofuranyl)acetic acid is separated and then reacted with sodium acetate trihydrate in methanol for 0.5 to 2 hours at reflux. (D)-α-Amino(2,3-dihydro-5-benzofuranyl)acetic acid is recovered.

The preferred compounds of this invention are compounds of formula 1 wherein W is hydrogen, amino, hydroxyl, carboxyl and sulfo; $R_1$ is hydrogen; $R_2$ is hydrogen, acetyloxy or heterocyclic thio and $R_3$ is hydrogen and the optical isomers thereof wherein the asymetric carbon atom of the 7-α-aminoacetamido group is in the (D) configuration.

More preferred are those compounds of formula 1 in which W is amino, $R_1$ is hydrogen, $R_2$ is hydrogen, acetyloxy, 5-methyl-1,3,4-thiadiazol-2-ylthio and 1,2,3-triazol-5-ylthio and $R_3$ is hydrogen and wherein the α-asymetric carbon atom of the 7-acetamido group is in the D-configuration.

The most preferred compound of this invention is the compound of formula 1 wherein $R_1$, $R_2$ and $R_3$ are hydrogen and W is amino and the α-asymetric carbon atom of the 7-acetamido group is in the D-configuration.

The daily dosage of the active ingredient may range from 1 mg to about 500 mg. The exact amount will vary with the patient's size, age and type of infection.

A typical tablet can have the following composition:
7-[[D-α-amino(2,3-dihydro-5-benzofuranyl)-actyl-]amino]-3-methyl-8-oxo-5-thia-1-azabicyclo[4.2.-0]oct-2-ene-2-carboxylic acid:50 mg
Lactose, USP:250 mg
Cornstarch, USP:50 mg
Cornstarch, USP (as 10% starch paste):5 mg
Calcium Stearate:2 mg The cephalosporin derivative, lactose and cornstarch are mixed and ground through a number 12 screen. The ground material is mixed with additional cornstarch as 10% starch paste and calcium stearate. Suitable size tablets can be prepared using a 5/16 inch diameter standard concave punch.

A typical parenteral solution may have the following composition:
7-[[D-α-amino(2,3-dihydro-5-benzofuranyl)-actyl-]amino]-3-methyl-8-oxo-5-thia-1-azabicyclo[4.2.-0]oct-2-ene-2-carboxylic acid:1.0 g
White beeswax:1.0 g
Peanut Oil, to make:10.0 cc Melt wax into a portion of the peanut oil and then add the remaining oil to the mix. Sterilize the mix at 150° C. for 2 hours with dry heat. Under sterile conditions mix the cephalosporin into the wax-oil mixture and place in an ampule and seal said ampule. For use, dilute contents of ampule with 10 cc of pure water and shake well. Each cc contains 50 mg of the cephalosporin compound.

A typical ointment can have the following composition:
7-[[D-α-Amino(2,3-dihydro-5-benzofuranyl)-actyl-]amino]-3-methyl-8-oxo-5-thia-1-azabicyclo[4.2.-0]oct-2-ene-2-carboxlic acid, sodium salt:50 mg/gram of ointment
Hydrophilic Base:
Cetyl alcohol:15%
White Wax:1%
Sodium Lauryl sulfate:2%
Propylene glycol:10%
Water:72%

Add the cephalosporin derivative to a small amount of water and incorporate into the base.

EXAMPLE 1

3-(Acetyloxy)methyl-7-amino-8-oxo-5-thia-1-azabicyclo[4.2.0]oct-2-ene-2-carboxylic acid tert-butyl ester 3-(Acetyloxy)methyl-7-amino-8-oxo-5-thia-1-azabicyclo [4.2.0]oct-2-ene-2-carboxylic acid (0.04 mole) is added to 100 ml of dioxane, 10 ml of concentrated sulfuric acid and 50 ml of liquid isobutylene in a pressure bottle. The mixture is shaken overnight. The bottle is chilled, opened and the contents poured into ice cold solution of sodium bicarbonate. Extraction of the aqueous phase with ethyl acetate followed by drying and evaporation of the ethyl acetate phase gives the tertbutyl ester, m.p. 111–112° C. See *J. Med. Chem.*, 9, 444 (1966).

In like manner using sufficient quantities of 7-amino-3-methyl-8-oxo-5-thia-1-azabicyclo[4.2.0]oct-2-ene-2-carboxylic acid and 7-amino-3-[[(5-methyl-1,3,4-thiadiazol-2-yl)thio]methyl]-8-oxo-5-thia-1azabicyclo-[4.2.0]oct-2-ene-2-carboxylic acid in place of 3-[(acetyloxy)methyl]-7-amino-8-oxo-5-thia-1-azabicyclo-[4.2.0]oct-2-ene-2-carboxylic acid, the corresponding tert-butyl esters are prepared respectively:

7-amino-3-methyl-8-oxo-5-thia-1-azabicyclo[4.2.-0]oct-2-ene-2-carboxylic acid tert-butyl ester, and
7-amino-3-[[(5-methyl-1,3,4-thiadiazol-2-yl)thio]methyl]-8-oxo-5-thia-1-azabicyclo[4.2.0]oct-2-ene-2-carboxylic acid tert-butyl ester.

EXAMPLE 2

α-Amino(2,3-dihydro-5-benzofuranyl)acetic acid 2,3-Dihydrobenzofuran (4.8 g, 40 mmole) is stirred with 9.0 g (40 mmole) of α-hydroxy-hippuric acid in 200 ml of 10% $H_2SO_4$-90% acetic acid mixture. The reaction is run at room temperature for 0.5 hour. After the half-hour, the reaction mixture is poured into 500 ml of water. The aqueous solution is extracted with ethyl acetate (4×100 ml). The ethyl acetate extracts are dried over magnesium sulfate and then evaporated to give α-benzamido(2,3-dihydro-5-benzofuranyl)acetic acid. Recrystallization of the crude benzamido compound from hexanemethylene chloride gives 11.56 g (94% yield).

The α-benzamido(2,3-dihydro-5-benzofuranyl)acetic acid (100 mg) is dissolved in 20 ml of methanol and 40 ml of water. Then 20 mg of a palladium on carbon catalyst is added and the mixture subjected to hydrogen pressure of 10 to 40 pounds/$in^2$ for 4 hours. The mixture is filtered to remove the solid and the methanol is evaporated to give the title compound in about 60% yield. NMR(DMSO-$D_6$)ppm(δ)7.95(s,1);6.7(m,3); 4.8(s,1);4.42(t,2);2.95(t,2).

EXAMPLE 3

α-(Tert-butoxycarbonyl)amino(2,3-dihydro-5-benzofuranyl)-acetic acid

α-Amino(2,3-dihydro-5-benzofuranyl)acetic acid (192 mg, 1 mmole) is added to 10 ml of 1:1 dioxane-water mixture with 4 mM of triethylamine and 0.17 ml of tert-butoxycarbonylazide. This mixture is stirred overnight at room temperature. The mixture is diluted with water and extracted with chloroform. The chloroform is dried and evaporated. The residue is taken up in ethyl acetate and washed with dilute aqueous hydrochloric acid. The organic layer is dried over magnesium sulfate and evaporated to give the title compound in a yield of about 80%.

NMR(CDCl$_3$)ppm($\delta$)10.4($\delta$,1); 6.87(m,3); 5.5(broad, 1);5.15(broad, 1); 4.6(t,2); 3.17(t,2); 1.35(s,9).

The identical procedure was used to prepare (D)-$\alpha$-(tert-butoxycarbonyl)amino(2,3-dihydro-5-benzofuranyl9-acetic acid from (D)-$\alpha$-(amino(2,3-dihydro-5-benzofuranyl)-acetic acid.

EXAMPLE 4

$\alpha$-Hydroxy(2,3-dihydro-5-benzofuranyl)acetic acid $\alpha$-Amino(2,3-dihydro-5-benzofuranyl)acetic acid (200 mg, 1.04 mmole) is dissolved in 250 mg (4.14 mmole) of glacial acetic acid and 145 mg (2.08 mmole) of sodium nitrite in about 5 ml of water is added dropwise. An additional 1 ml of glacial acetic acid is added and the mixture is heated to 65° C. and held at 65° C. for 4 hours. After cooling the reaction mixture is diluted with water and extracted with ethyl acetate for several hours. The ethyl acetate is dried over magnesium sulfate, filtered and evaporated to give a 65% yield of the title compound. NMR(DMSO-D$_6$)ppm($\delta$)7.15(m,3); 5.18(d,1); 4.78(t,2) and 3.34(t,2).

EXAMPLE 5

(2,3-Dihydro-5-benzofuranyl)acetic acid $\alpha$-Hydroxy(2,3-dihydro-5-benzofuranyl)acetic acid (10 mmole) is added to ethyl alcohol (20 ml) containing about 1 ml of concentrated sulfuric acid and the mixture heated for 2 hours. Approximately half of the alcohol is removed, the remainder of the mixture is poured into about 160 ml of water. The aqueous mixture is extracted with chloroform, the chloroform is dried and the solvents are removed. The residue is used without further purification.

The ester prepared above (10 mmole) is added to about 25 ml of ether containing an acid acceptor such as triethylamine. Then acetyl chloride (10 mmole) is slowly added to the ether solution which begins to reflux from the liberated heat. After stirring for 0.5 hour the solvents are removed and $\alpha$-acetyloxy(2,3-dihydro-5-benzofuranyl)acetic acid ethyl ester is recovered as the residue.

The acetylated hydroxy ester (10 mmole) is dissolved in 40 ml of methanol to which is added about 50 mg of a palladium on carbon catalyst. The mixture is subjected to 40 pounds/in$^2$ of hydrogen pressure for 4 hours. At the end of this time the mixture is filtered to remove the catalyst and the solvent is removed. The residue, (2,3-dihydro-5-benzofuranyl)acetic acid, ethyl ester is dissolved in methanol and a 10% excess of sodium hydroxide is added. The mixture is refluxed for about 60 minutes and the solvent removed by evaporation. The residue is taken up in water and the pH adjusted to about 2 with hydrochloric acid. The title compond precipiates from solution and is recovered by filtration.

EXAMPLE 6

2-(2,3-Dihydro-5-benzofuranyl)malonic acid

To a solution of diisopropylamide (20 mmole) in 50 ml of anhydrous tetrahydrofuran (THF) maintained under a nitrogen atmosphere at $-40°$ C. is added n-butyllithium (20 mmole). The mixture is stirred for 15 minutes and then (2,3-dihydro-5-benzofuranyl)acetic acid (10 mmole) is added. The mixture is heated at 50° C. for 1 hour and then cooled to $-70°$ C. and ethyl chloroformate (10 mmole) is added. The temperature is increased and the mixture is stirred for about 20 minutes. The mixture is poured over ice and hydrochloric acid. The aqueous phase is extracted with ether. The ether extracts are combined, dried and evaporated to give 2-(2,3-dihydro-5-benzofuranyl)malonic acid, monoethyl ester.

The monoethyl ester of 2-(2,3-dihydro-5-benzofuranyl)-malonic acid (10 mmole) is added to methanol containing 11 mmole of sodium hydroxide. The mixture is refluxed for about 30 minutes and then the methanol is removed. The residue is taken up in water. Adjustment of the pH to 2 with hydrochloric acid results in the precipitation of the title acid. The title compound is filtered and dried.

EXAMPLE 7

$\alpha$-Sulfo(2,3-dihydro-5-benzofuranyl)acetic acid

The title compound is prepared by a modification of the procedure described in *J. Am. Chem. Soc.*, 75, 1653 (1953). To a solution of ethylene chloride is added about 15 mmole of the dioxane-sulfur trioxide reagent and the temperature of the mixture warms to room temperature. (2,3-Dihydro-5-benzofuranyl)acetic acid (10 mmole) is added over a period of 30 minutes. The solution is stirred overnight at about 10° C. and then poured into cold water. The organic layer is separated and extracted with water. The aqueous extracts are combined with the water layer which is neutralized with sodium hydroxide and evaporated to dryness. The residue is extracted with 70% ethanol. Concentrating the alcohol solution and subsequent cooling gives the sodium salt of 60-sulfo(2,3-dihydro-5-benzofuranyl)acetic acid. Treatment of the sodium salt with hydrochloric acid followed by recrystallization of the acid from ethanol gives the title compound.

EXAMPLE 8

D-$\alpha$-Amino(2,3-dihydro-5-benzofuranyl)acetic acid

The resolving agent, binaphthyl phosphoric acid (BPA), is described in *Tetrahedron Letters,* 1971, 4617.

A racemic mixture of (D,L)-$\alpha$-amino(2,3-dihydro-5-benzofuranyl)acetic acid is prepared according to the procedure in Example 2. The racemic mixture, 2.7 g (13.99 mmole), is treated with 3.5 g (10 mmole) of (+)-binaphthyl phosphoric acid (BPA) and 4 mmole of hydrochloric acid in 25 ml of methanol. This mixture is refluxed for 30 minutes. After cooling to 0° C., the salt formed between (+)-BPA and D-$\alpha$-amino(2,3-dihydro-5-benzofuranyl)acetic acid precipitates and is filtered. A total of 2.76 g (51%) of salt is obtained.

The BPA-D-$\alpha$-amino(2,3-dihydro-5-benzofuranyl)acetic acid salt (2.76 g, 5.1 mmole) is slurried in 50 ml of methanol. Sodium acetate trihydrate (0.691 g, 5.1 mmole) is added and the mixture is refluxed for 1 hour. The hot solution is filtered and the solid is washed with hot methanol to give 0.88 g (90%) of D-$\alpha$-amino(2,3-dihydro-5-benzofuranyl)acetic acid, $[\alpha]_D^{20} = -131°$ C.

EXAMPLE 9

7-[[D-α-(tert-Butoxycarbonyl)amino(2,3-dihydro-5-benzofuranyl)acetyl]amino]-3-methyl-8-oxo-5-thia-1-azabicyclo-[4.2.0]oct-2-ene-2-carboxylic acid, tert-butyl ester

D-α-(tert-Butoxycarbonyl)amino(2,3-dihydro-5-benzofuranyl)acetic acid (1.16 g, 3.96 mmole), 1.069 g (3.96 mmole) of 7-amino-3-methyl-8-oxo-5-thia-1-azabicyclo[4.2.0]oct-2-ene-2-carboxylic acid, tert-butyl ester and 0.978 g (3.96 mmole) of N-ethoxycarbonyl-2-ethoxy-1,2-dihydroquinoline (EEDQ) are mixed in 50 ml of hydrocarbon stabilized chloroform. The mixture is stirred overnight at room temperature under a nitrogen atmosphere. The reaction mixture is diluted with chloroform, washed with dilute aqueous hydrochloric acid, dilute aqueous sodium bicarbonate and water. The chloroform solution is dried over magnesium sulfate, filtered and evaporated to dryness to give 3.3 g of solid. This material is subjected to high pressure chromotography using 20% hexane in chloroform. About 2.4 g of the title compound is obtained. NMR(DMSO-D$_6$)ppm($\delta$)7.05(m,4); 5.85(q,2); 5.3(d,1); 5.01(d,1); 4.67(t,2); 3.32(m,4); 2.18(s,3); 1.70(s,9) and 1.60(s,9).

Substitution of a racemic mixture of α-(tert-butoxycarbonyl)amino(2,3-dihydro-5-benzofuranyl)acetic acid, tert-butyl ester for D-α-(tert-butoxycarbonyl)amino(2,3-dihydro-5-benzofuranyl)acetic acid, tert-butyl ester in the above preparation gives the corresponding cephalosporin derivative.

In like manner substituting 3-[(acetyloxy)methyl]-7-amino-7-methoxy-8-oxo-5-thia-1-azabicyclo[4.2.0]oct-2-ene-2-carboxylic acid, tert-butyl ester and 7-amino-3-[[(1-methyltetrazol-5-yl)thio]methyl]-8-oxo-5-thia-1-azabicyclo[4.2.0]oct-2-ene-2-carboxylic acid, tert-butyl ester for 7-amino-3-methyl-8-oxo-5-thia-1-azabicyclo-[4.2.0]oct-2-ene-2-carboxylic acid, tert-butyl ester gives the following compounds:

3-[(acetyloxy)methyl]-7-[[(tert-butoxycarbonyl)amino(2,3-dihydro-5-benzofuranyl)acetyl]amino]-7-methoxy-8-oxo-5-thia-1-azabicyclo[4.2.0]oct-2-ene-2-carboxylic acid, tert-butyl ester, and 7-[[(tert-butoxycarbonyl)amino(2,3-dihydro-5-benzofuranyl)-acetyl]amino]-3-[[(1-methyltetrazol-5-yl)thio]methyl]-8-oxo-5-thia-1-azabicyclo[4.2.-0]oct-2-ene-2-carboxylic acid, tert-butyl ester.

EXAMPLE 10

7-[[Amino(2,3-dihydro-5-benzofuranyl)acetyl]amino]3-methyl-8-oxo-5-thia-1-azabicyclo[4.2.0]oct-2-ene-2-carboxylic acid

7-[[(tert-Butoxycarbonyl)amino(2,3-dihydro-5-benzofuranyl)acetyl]amino]-3-methyl-8-oxo-5-thia-1-azabicyclo[4.2.0]oct-2-ene-2-carboxylic acid, tert-butyl ester (2.4 g, 4.4 mmole) is added to 10 ml of trifluoroacetic acid (TFA). The mixture is stirred for 10 minutes at room temperature and the TFA is removed under reduced pressure. The residue is dissolved in methanol and a large excess of ether is added. The white precipitate is the TFA salt of 7-[[amino(2,3-dihydro-5-benzofuranyl)acetyl]amino]-3-methyl-8-oxo-5-thia-1-azabicyclo-[4.2.0]oct-2-ene-2-carboxylic acid.

The TFA salt (0.72 g, 1.43 mmole) is dissolved in 10 ml of water and 0.12 (1.43 mmole) of sodium bicarbonate in about 10 ml of water is slowly added while monitoring the pH of the mixture. Material begins precipitating from solution at pH=4.5. When all of the bicarbonate is added, the pH is about 6.5. The title compound is recovered by filtration and is washed with water. The dried material has an M.P. of 190°-195° C.

In like manner and substituting 3-[(acetyloxy)-methyl]-7-[[(tert-butoxycarbonyl)amino(2,3-dihydro-5-benzofuranyl)acetyl]amino]-7-methoxy-8-oxo-5-thia-1-azabicyclo[4.2.0]oct-2-ene-2-carboxylic acid, tert-butyl ester, and 7-[[(tert-butoxycarbonyl)amino(2,3-dihydrobenzofuranyl)acetyl]amino]-3-[[(1-methyltetrazol-5-yl)-thio]methyl]-8-oxo-5-thia-1-azabicyclo[4.2.0]oct-2-ene- 2-carboxylic acid, tert-butyl ester gives:

3-[(acetyloxy)methyl]-7-[[amino(2,3-dihydro-5-benzofuranyl)acetyl]amino]-7-methoxy-8-oxo-5-thia-1-azabicyclo-[4.2.0]oct-2-ene-2-carboxylic acid, and 7-[[amino(2,3-dihydro-5-benzofuranyl)acetyl]amino]-3-[[(1-methyltetrazol-5-yl)thio]methyl]-8-oxo-5-thia-1-azabicyclo[4.2.0]oct-2-ene-2-carboxylic acid.

EXAMPLE 11

3-[(Acetyloxy)methyl]-7-[[D-α-amino(2,3-dihydro-5-benzofuranyl)acetyl]amino]-8-oxo-5-thia-1-azabicyclo[4.2.0]-oct-2-ene-2-carboxylic acid

A solution of D-α-(tert-butoxycarbonyl)amino(2,3-dihydro-5-benzofuranyl)acetic acid (20 mmole) and triethylamine (20 mmole) in 80 ml of tetrahydrofuran (THF) is cooled to about 0° C. While stirring, isobutyl chloroformate (20 mmole) is added and the temperature maintained at 0° C. for 15 minutes. A cold solution of 3-[(acetyloxy)-methyl]-7-amino-8-oxo-5-thia-1-azabicyclo[4.2.0]oct-2-ene-2-carboxylic acid (20 mmole) and 20 mmole of triethylamine in 72 ml of 50% aqueous THF is added to the previously prepared solution. The mixture is stirred at 5° C. for about 1 hour and then for 1 hour at room temperature. The THF is evaporated and the residue is dissolved in water and washed with ethyl acetate. The aqueous phase is covered with a fresh layer of ethyl acetate, cooled in an ice bath and acidified to a pH of 3 with 6N hydrochloric acid. The mixture is filtered and the ethyl acetate separated. The aqueous phase is washed with fresh ethyl acetate. The combined ethyl acetate fractions are dried over magnesium sulfate, treated with charcoal, filtered and concentrated. The concentrate is then added with vigorous stirring to a mixture of ether-hexane. 3-[(Acetyloxy)methyl]-7-[[D-α-(tert-butoxycarbonyl)amino-(2,3-dihydro-5-benzofuranyl)acetyl]amino]-8-oxo-5-thia-1-azabicyclo[4.2.0]oct-2-ene-2-carboxylic acid is recovered by filtration. This solid (5 mmole) is then treated according to the method described in Example 10 to hydrolyze the tert-butoxycarbonyl group and to form the monotrifluoroacetic acid salt. This material decomposes when a melting point is taken. Subsequent neutralization of the trifluoroacetic acid salt (Example 10) gives the title compound.

In like manner and substituting 7-amino-7-methoxy-3-methyl-8-oxo-5-thia-1-azabicyclo[4.2.0]oct-2-ene-2-carboxylic acid or 7-amino-3-[[(1-methyltetrazol-5-yl)-thio]methyl]-8-oxo-5-thia-1-azabicyclo[4.2.0]oct-2-ene-2-carboxylic acid in place of 3-[(acetyloxy)methyl]-7-amino-8-oxo-5-thia-1-azabicyclo[4.2.0]oct-2-ene-2-carboxylic acid give respectively the following:

7-[[D-α-amino(2,3-dihydro-5-benzofuranyl)acetyl]amino]-7-methoxy-3-methyl-8-oxo-5-thia-1-azabicyclo[4.2.0]oct-2-ene-2-carboxylic acid, and 7-[[D-α-amino(2,3-dihydro-5-benzofuranyl)acetyl]amino]-3-[[(1-methyltetrazol-5-yl)thio]methyl]-8- oxo-5-thia-1-azabicyclo[4.2.0]oct-2-ene-2-carboxylic acid.

EXAMPLE 12

7-[[D-α-(tert-Butoxycarbonyl)amino(2,3-dihydro-5-benzofuranyl)acetyl]amino]-3-methyl-8-oxo-5-thia-1-azabicyclo-[4.2.0]oct-2-ene-2-carboxylic acid, tert-butyl ester D-α-(tert-Butoxycarbonyl)amino(2,3-dihydro-5-benzofuranyl)acetic acid in tetrahydrofuran (THF) is cooled to 0° C. and 20 mmole of dicyclohexylcarbodiimide is added in one portion. This mixture at 0° C. is stirred for 5 minutes and then 7-amino-3-methyl-8-oxo-5-thia-1-azabicyclo[4.2.0]oct-2-ene-2-carboxylic acid, tert-butyl ester (20 mmole) is added. The temperature is maintained at 0° C. for 1 hour and then raised to 20° C. The mixture is stirred for 18 hours at 20° C. The mixture is filtered to remove solids and the THF is then removed under reduced pressure. The residue is taken up in ethyl acetate which is extracted with aqueous sodium bicarbonate and then with water. The ethyl acetate solution is dried over magnesium sulfate and then evaporated to give the title compound.

If desired the protecting groups may be removed using the procedure of Example 10.

In like manner and substituting 7-amino-7-methoxy-3-[[(5-methyl-1,3,4-thiadiazol-2-yl)thio]methyl]-8-oxo-5-thia-1-azabicyclo[4.2.0]oct-2-ene-2-carboxylic acid, tert-butyl ester or 7-amino-3-[[(1-methyltetrazol-5-yl)thio]methyl]-8-oxo-5-thia-1-azabicyclo[4.2.0]oct-2-ene-2-carboxylic acid, tert-butyl ester for 7-amino-3-methyl-8-oxo-5-thia-1-azabicyclo[4.2.0]oct-2-ene-2-carboxylic acid, tert-butyl ester gives respectively:

7-[[D-α-(tert-Butoxycarbonyl)amino(2,3-dihydro-5-benzofuranyl)acetyl]amino]-7-methoxy-3-[[(5-methyl-1,3,4-thiadiazol-2-yl)thio]methyl]-8-oxo-5-thia-1-azabicyclo[4.2.0]oct-2-ene-2-carboxylic acid, tert-butyl ester, or 7-[[D-α-(tert-Butoxycarbonyl)amino(2,3-dihydro-5-benzofuranyl)acetyl]amino]-3-[[(1-methyltetrazol-5-yl)thio]methyl]-8-oxo-5-thia-1-azabicyclo[4.2.0]oct-2-ene-2-carboxylic acid, tert-butyl ester.

EXAMPLE 13

3-[(Acetyloxy)methyl]-7-[[sulfo(2,3-dihydro-5-benzofuranyl)acetyl]amino]-8-oxo-5-thia-1-azabicyclo[4.2.0]oct-2-ene-2-carboxylic acid α-Sulfo(2,3-dihydro-5-benzofuranyl)acetyl chloride is prepared according to the general method described in *J. Med. Chem.*, 15, 1105 (1972). α-Sulfo(2,3-dihydro-5-benzofuranyl)acetic acid 20 mmole is added slowly to a solution of diethyl ether (4 ml) and thionyl chloride (150 mmole). The mixture is stirred at room temperature until the gas evolution stops. Then about 0.2 ml of dimethylformamide is added and the solution heated at 40° C. for 4 hours. The mixture is diluted with 30 ml of diethyl ether and 30 ml of hexane and then cooled to about −25° C. The α-sulfo(2,3-dihydro-5-benzofuranyl)acetyl chloride is recovered from the mixture and used without further purification.

α-Sulfo(2,3-dihydro-5-benzofurayl)acetyl chloride (5 mmole) in 10 ml of ether is added to 5 mmole of 3-[(acetyloxy)methyl]-7-amino-8-oxo-5-thia-1-azabicyclo[4.2.0]oct-2-ene-2-carboxylic acid dissolved in 10 ml of water containing 10 mmole of sodium bicarbonate. The temperature is maintained at about 0° C. during the addition. The reaction mixture is stirred for about 30 minutes at 0° C. The organic phase is separated from the aqueous phase. The pH of the aqueous phase is adjusted to 6.5 to 7.0. The aqueous phase is extracted with ethyl acetate. The ethyl acetate is dried over magnesium sulfate, filtered and evaporated to give the title compound.

In like manner and substituting 3-(acetyloxy)methyl-7-amino-7-methoxy-8-oxo-5-thia-1-azabicyclo[4.2.0]oct-2-ene-2-carboxylic acid and 7-amino-3-[[(1-methyltetrazol-5-yl)thio]methyl]-8-oxo-5-thia-1-azabicyclo[4.2.0]oct-2-ene-2-carboxylic acid for 3-[(acetyloxy)methyl]-7-amino-8-oxo-5-thia-1-azabicyclo[4.2.0]oct-2-ene-2-carboxylic acid gives respectively:

3-[(acetyloxy)methyl]-7-[[sulfo(2,3-dihydro-5-benzofurnanyl)acetyl]amino]-7-methoxy-8-oxo-5-thia-1-azabicyclo[4.2.0]oct-2-ene-2-carboxylic acid, and 7-[[sulfo(2,3-dihydro-5-benzofuranyl)acetyl]amino]-3-[[(1-methyltetrazol-5-yl)thio]methyl]-8-oxo-5-thia-1-azabicyclo[4.2.0]oct-2-ene-2-carboxylic acid.

EXAMPLE 14

3-[(Acetyloxy)methyl]-7-[[(2,3-dihydro-5-benzofuranyl)-hydroxyacetyl]amino]-8-oxo-5-thia-1-azabicyclo[4.2.0]oct-2-ene-2-carboxylic acid α-Hydroxy-(2,3-dihydro-5-benzofuranyl)acetic acid (10 mmole) triethylamine (10 mmole) and bistrimethylsilylacetamide (BSA) (10 mmole) are added to 50 ml of THF and refluxed for two hours. The reaction mixture is cooled to about −10° C. and 10 mmole of isobutyl chloroformate is added dropwise. After 30 minutes at −10° C., 10 mmole of 3-[(acetyloxy)methyl]-7-amino-8-oxo-5-thia-1-azabicyclo[4.2.0]oct-2-ene-2-carboxylic acid in 50 ml of water—20 ml of THF containing 10 mmole of triethylamine is added dropwise to the cooled reaction mixture. The temperature is maintained between −10° C. and 0° C. during the addition. The reaction mixture is allowed to come to room temperature very slowly. About 50 cc of saturated aqueous sodium bicarbonate and 100 ml of water are added to the reaction mixture. This mixture is treated several times with ether which is then discarded. The aqueous phase is layered with ethyl acetate and the pH of the aqueous solution is adjusted to 1.5. The ethyl acetate is then separated from the aqueous phase, dried over magnesium sulfate, filtered and evaporated to give the title compound.

In a similar manner, substitution of 7-amino-3-[[(1-methyltetrazol-5-yl)thio]methyl]-8-oxo-5-thia-1-azabicyclo[4.2.0]oct-2-ene-2-carboxylic acid for 3-[(acetyloxy)methyl]-7-amino-8-oxo-5-thia-1-azabicyclo-[4.2.0]oct-2-ene-2-carboxylic acid gives 7[[(2,3-dihydro-5-benzofuranyl)hydroxyacetyl]amino]-3-[[(1-methyltetrazol-5-yl)thio]methyl]-8-oxo-5-thia-1-azabicyclo[4.2.0]oct-2-ene-2-carboxylic acid.

EXAMPLE 15

3-[(Acetyloxy)methyl]-7-[[(2,3-dihydro-5-benzofuranyl)-acetyl]amino]-8-oxo-5-thia-1-azabicyclo[4.2.0]oct-2-ene-2-carboxylic acid A solution of 10 mmole of 2,3-dihydo-5-benzofuranyl acetic acid and 10 mmole of triethylamine in 100 ml of THF is cooled to about 0° C. While stirring, isobutylchloroformate (10 mmole) is added and the temperature maintained at 0° C. for 15 minutes. A cold solution of 3-[(acetyloxy)methyl]-7-amino-8-oxo-5-thia-1-azabicyclo[4.2.0]oct-2-ene-2-carboxylic acid (10 mmole) and 10 mmole of triethylamine in 80 ml of 50% aqueous THF is added to the previously prepared solution. The mixture is stirred at 5° C. for 1 hour and at room temperature for 1 hour. Then the THF is evaporated and the residue is dissolved in water and washed with ethyl acetate. The aqueous phase is covered with ethyl acetate and the pH is adjusted to 3 with 6N hydrochloric acid. The mixture is filtered and the layers separated. The ethyl acetate is dried over magnesium sulfate, filtered and evaporated to give the title compound.

In like manner substitution of 2-(2,3-dihydro-5-furanyl)malonic acid, monoethyl ester for 2,3-dihydro-5-benzofuranyl acetic acid gives 3-[(acetyloxy)methyl]-7-[[(3-ethoxy-1,3-dioxo-2-(2,3-dihydro-5-benzofuranyl)propyl]amino]-9-oxo-5-thia-1-azabicylo[4.2.0]oct-2-ene-2-carboxylic acid.

EXAMPLE 16

3-[(Acetyloxy)methyl]-7-[[carboxy(2,3-dihydro-5-benzofuranyl)acetyl]amino]-8-oxo-5-thia-1-azabicyclo[4.2.-0]oct-2-ene-2-carboxylic acid The title compound is prepared according to the general procedure described in Example 3 of U.S. Pat. No. 3,282,926.

α-Carboxy-(2,3-dihydro-5-benzofuranyl)acetic acid (14 mmole) is added to 50 ml of ether. Thionyl chloride (14.5 mmole) is added along with 1 drop of dimethylformamide. This mixture is refluxed about 3 hours and then evaporated under reduced pressure at room temperature. The residue is added to 50 ml of ether which is added to an ice-cold mixture of 3-[(acetyloxy)methyl]-7-amino-8-oxo-5-thia-1-azabicyclo[4.2.0]oct-2-ene-2-carboxylic acid (14 mmole), 30 ml of water 15 ml of ether, 14 mmole of triethylamine. After 30 minutes the pH is adjusted to 1.5 with dilute hydrochloric acid and the layers separated. The ether is extracted with water. Evaporation of the ether gives a residue which is taken up in ethyl acetate, dried, filtered and evaporated to give the title compound.

Substitution of 7-amino-3-[[(5-methyl-1,3,4-thiadiazol-2-yl)thio]methyl]-8-oxo-5-thia-1-azabicyclo[4.2.0]oct-2-ene-2-carboxylic acid for 3-[(acetyloxy)methyl]-7-amino-8-oxo-5-thia-1-azabicyclo[4.2.0]oct-2-ene-2-carboxylic acid gives 7-[[(carboxy(2,3-dihydro-5-benzofuranyl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid.

EXAMPLE 17

3-[(Acetyloxy)methyl]-7-[[3-ethoxy-1,3-dioxo-2-(2,3-dihydro-5-benzofuranyl)propyl]amino]-8-oxo-5-thia-1-azabicyclo[4.2.0]oct-2-ene-2-carboxylic acid p-(acetyloxy)benzyl ester To a suspension of 6 mmole of 3-[(acetyloxy)methyl]-7-[[3-ethoxy-1,3-dioxo-2-(2,3-dihydro-5-benzofuranyl)-propyl]amino]-8-oxo-5-thia-1-azabicyclo[4.2.0]oct-2-ene-2-carboxylic acid, sodium salt in 40 ml of dimethylformamide (DMF) is added 2 equivalents of p-(acetyloxy)-benzyl alcohol. The mixture is cooled to 0° C. after which 6.8 mM of dicyclohexylcarbodiimide in 10 ml of DMF is added dropwise with stirring. The mixture is stirred at 0° C. for 1 hour and an addition 4 hours at room temperature. Dicyclohexylurea is removed by filtration. The filtrate is diluted with chloroform, washed with water, dried over magnesium sulfate, filtered and evaporated in vacuo to give the title compound.

When in the above procedure an appropriate amount of p-(propionyloxy)benzyl alcohol, p-(pivaoxyloxy)-benzyl alcohol or p-(butyryloxy)benzyl alcohol is substituted for p-(acetyloxy)benzyl alcohol the following respective products are obtained:

3-[(acetyloxy)methyl]-7-[[3-ethoxy-1,3-dioxo-2-(2,3-dihydro-5-benzofuranyl)propyl]amino]-8-oxo-5-thia-1-azabicyclo[4.2.0]oct-2-ene-2-carboxylic acid p-(propionyloxy)benzyl ester, 3-[(acetyloxy)methyl]-7-[[3-ethoxy-1,3-dioxo-2-(2,3-dihydro-5-benzofuranyl)propyl]amino]-8-oxo-5-thia-1-azabicyclo[4.2.0]oct-2-ene-2-carboxylic acid p-(pivaloyloxy)benzyl ester, and 3-[(acetyloxy)methyl]-7-[[3-ethoxy-1,3-dioxo-2-(2,3-dihydro-5-benzofuranyl)propyl]amino]-8-oxo-5-thia- 1-azabicyclo[4.2.0 ]oct-2-ene-2-carboxylic acid p-(butyryloxy)benzyl ester.

EXAMPLE 18

3-[(Acetyloxy)methyl]-7-[[(tert-butoxycarbonyl-)amino(2,3-dihydro-5-benzofuranyl)acetyl]amino]-8-oxo-5-thia-1-azabicyclo[4.2.0]oct-2-ene-2-carboxylic acid pivaloyloxymethyl ester To dimethylformamide is added the sodium salt of 3-[(acetyloxy)methyl]-7-[[(tert-butoxycarbonyl-)amino(2,3-dihydro-5-benzofuranyl)acetyl]amino]-8-oxo-5-thia-1-azabicyclo[4.2.0]oct-2-ene-2-carboxylic acid one equivalent, and the solution is stirred at room temperature for about 30 minutes after which an equivalent of chloromethylpivalate is added. Stirring is continued for about 3 hours. The solution is diluted with ethyl acetate and washed with water. The organic layer is separated and evaporated to dryness. The residue is recrystallized from ethyl acetate to give the title compound.

In a similar manner when an appropriate amount of chloromethylpropionate, chloromethylacetate or chloromethylbutyrate is substituted for the chloromethylpivalate, the following respective products are obtained:

3-[(acetyloxy)methyl]-7-[[(tert-butoxycarbonyl-)amino(2,3-dihydro-5-benzofuranyl)acetyl]amino]-8-oxo-5-thia-1-azabichclo[4.2.0]oct-2-ene-2-carboxylic acid propionyloxymethyl ester, 3-[(acetyloxy)methyl]-7-[[(tert-butoxycarbonyl-)amino(2,3-dihydro-5-benzofuranyl)acetyl]amino]-8-oxo-5-thia-1-azabicyclo[4.2.0]oct-2-ene-2-carboxylic acid acetyloxymethyl ester; and 3-[(acetyloxy)methyl]-7-[[(tert-butoxycarbonyl-)amino(2,3-dihydro-5-benzofurayl)acetyl]amino]-8-oxo-5-thia-1-azabicyclo[4.2.0]oct-2-ene-2-carboxylic acid butyryloxymethyl ester.

EXAMPLE 19

3-[(Acetyloxy)methyl-7-[[(tert-butoxycarbonyl-)amino)2,3-dihydro-5-benzofuranyl)acetyl]amino]-8-oxo-5-thia-1-azabicyclo[4.2.0]oct-2-ene-2-carboxylic acid N-butyrylaminomethyl ester To dimethylformamide is added the sodium salt of 3-[(acetyloxy)methyl]-7-[[(tert-butoxycarbonyl-)amino(2,3-dihydro-5-benzofuranyl)acetyl]amino]-8-oxo-5-thia-1-azabicyclo[4.2.0]oct-2-ene-2-carboxylic acid, one equivalent, and an equivalent amount of N-butyrylaminomethyl chloride. The mixture is stirred at room temperature for about one hour after which it is carefully poured into ice water. The product precipitates and is recovered by filtration. The solid is dissolved in ethyl acetate and washed with aqueous sodium bicarbonate and then with water. The organic layer is dried over magnesium sulfate, filtered and evaporated to dryness in vacuo to give the title compound.

In like manner and when using the appropriate quantity of N-methyl-N-butyrylaminomethyl chloride or N-acetylaminomethyl chloride for N-butyrylaminomethyl chloride the following respective compounds are obtained:

3-[(acetyloxy)methyl]-7-[[(tert-butoxycarbonyl)amino(2,3-dihydro-5-benzofuranyl)acetyl]amino]-8-oxo-5-thia-1-azabicyclo[4.2.0]oct-2-ene-2-carboxylic acid N-methyl-N-butyrylaminomethyl ester, and 3-[(acetyloxy)methyl]-7-[[(tert-butoxycarbonyl)amino(2,3-dihydro-5-benzofuranyl)acetyl]amino]-8-oxo-5-thia-1-azabicyclo[4.2.0]oct-2-ene-2-carboxylic acid N-acetylaminomethyl ester.

EXAMPLE 20

7-[[(2,3-dihydro-5-benzofuranyl)acetyl]amino]-3-[[1-methyltetrazol-5-yl)thio]methyl]-8-oxo-5-thia-1-azabicyclo[4.2.0]oct-2-ene-2-carboxylic acid 2-amino-3methylbutyryloxymethyl ester A suspension of 50 mmole of 7-[[(2,3-dihydro-5-benzofuranyl)acetyl]amino]-3-[[(1-methyltetrazol-5-yl)thio]methyl]-8-oxo-5-thia-1-azabicyclo[4.2.0]oct-2-ene-2-carboxylic acid sodium salt and 50 mmole of N-tert-butoxycarbonyl-L-valine chloromethyl ester, prepared by the procedure described in W. German Offen. No. 2,236,620, are mixed in 100 ml of dimethylformamide and stirred for about 72 hours. The mixture is diluted with ethyl acetate, washed with water, with aqueous sodium bicarbonate, and with water a second time. The organic layer is dried over magnesium sulfate, filtered and evaporated to give 7-[[(2,3-dihydro-5-benzofuranyl)acetyl]amino]-3-[[(1-methyltetrazol-5-yl)thio]methyl]-8-oxo-5-thia-1-azabicyclo[4.2.0]oct-2-ene-2-carboxylic acid N-tert-butoxycarbonyl-2-amino-3-methylbutyrylmethyl ester from which the amine protecting group is removed by standard procedures to give the title compound.

EXAMPLE 21

3-[(Acetyloxy)methyl]-7-[[(tert-butoxycarbonyl)amino-(2,3-dihydro-5-benzofuranyl)acetyl]amino]-8-oxo-5-thia-1-azabicyclo[4.2.0]oct-2-ene-2-carboxylic acid N-ethoxycarbonyl-N-methylaminomethyl ester 3-[(Acetyloxy)methyl]-7-[[(tert-butoxycarbonyl)amino(2,3-dihydro-5-benzofuranyl)acetyl]amino]-8-oxo-5-thia-1-azabicyclo[4.2.0]oct-2-ene-2-carboxylic acid sodium salt, 3.0 mmole, in 60 ml of dimethylformamide is treated at room temperature with 3.0 mmole of N-chloromethyl-N-methylurethane for one hour. The mixture is carefully poured into ice water and the precipitated solid is removed by filtration and washed with water. The solid is dissolved in ethyl acetate and washed with aqueous sodium bicarbonate and then with water. The organic layer is dried over magnesium sulfate, filtered and evaporated to dryness in vacuo to give the title compound.

EXAMPLE 22

In the following table are listed compounds of this invention which are prepared by the procedures described in Examples 11, 13, 14 and 16.

TABLE 1

| Reactants | | Method | |
|---|---|---|---|
| 7-Aminocephalosporin | Acid | of Example | Product |
| 7-amino-3-[[(5-methyl-1,3,4-thiadiazol-2-yl)thio]methyl]-8-oxo-5-thia-1-azabicyclo[4.2.0]oct-2-ene-2-carboxylic acid | D-α-(tert-butoxycarbonyl)amino(2,3-dihydro-5-benzofuranyl)acetic acid | 11 | 7-[[D-α-amino(2,3-dihydro-5-benzofuranyl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid |
| 7-amino-3-[[(1,2,3-triazol-5-yl)thio]methyl]-8-oxo-5-thia-1-azabicyclo[4.2.0]oct-2-ene-2-carboxylic acid | D-α-(tert-butoxycarbonyl)amino(2,3-dihydro-5-benzofuranyl)acetic acid | 11 | 7-[[D-α-amino(2,3-dihydro-5-benzofuranyl)acetyl]amino]-3-[[(1,2,3-triazol-5-yl)thio]methyl]-8-oxo-5-thia-1-azabicyclo[4.2.0]oct-2-ene-2-carboxylic acid The trifluoroacetic acid salt has an M.P. of 160° C. |
| 7-amino-3-methyl-8-oxo-5-thia-1-azabicyclo[4.2.0]oct-2-ene-2-carboxylic acid | (2,3-dihydro-5-benzofuranyl)hydroxyacetic acid | 14 | 7-[[(2,3-dihydro-5-benzofuranyl)hydroxyacetyl]amino]-3-methyl-8-oxo-5-thia-1-azabicyclo[4.2.0]-oct-2-ene-2-carboxylic acid |
| 7-amino-3-[[(5-methyl-1,3,4-thiadiazol-2-yl)thio]methyl]-8-oxo-5-thia-1-azabicyclo[4.2.0]oct-2-ene-2-carboxylic acid | (2,3-dihydro-5-benzofuranyl)hydroxyacetic acid | 14 | 7-[[(2,3-dihydro-5-benzofuranyl)hydroxyacetyl]amino]-3-[[(5-methyl-1,3,4-thiadiazol-2-yl)thio]methyl]-8-oxo-5-thia-1-azabicyclo[4.2.0]oct-2-ene-2-carboxylic acid |
| 7-amino-3-[[(1,2,3-triazol-5-yl)thio]methyl]-8-oxo-5-thia-1-azabicyclo[4.2.0]oct-2-ene-2-carboxylic acid | (2,3-dihydro-5-benzofuranyl)hydroxyacetic acid | 14 | 7-[[(2,3-dihydro-5-benzofuranyl)hydroxyacetyl]amino]-3-[[(1,2,3-triazol-5-yl)thio]methyl]-8-oxo-5-thia-1-azabicyclo[4.2.0.]-oct-2-ene-2-ene-2-carboxylic acid |
| 7-amino-3-methyl-8-oxo-5-thia-1-azabicyclo[4.2.0]-oct-2-ene-2-carboxylic acid | α-Carboxy(2,3-dihydro-5-benzofuranyl)-acetic acid | 16 | 7-[[carboxy(2,3-dihydro-5-benzofuranyl)acetyl]amino]-3-methyl-8-oxo-5-thia-1-azabicyclo[4.2.0]oct-2-ene- |

TABLE 1-continued

| Reactants | | Method | |
|---|---|---|---|
| 7-Aminocephalosporin | Acid | of Example | Product |
| 7-amino-3-[[(1-methyl-tetrazol-5-yl)thio]-methyl]-8-oxo-5-thia-1-azabicyclo[4.2.0]oct-2-ene-2-carboxylic acid | α-Carboxy(2,3-dihydro-5-benzofuranyl)acetic acid | 16 | 2-carboxylic acid 7-[[carboxy(2,3-dihydro-5-benzofuranyl)acetyl]amino]-3-[[(1-methyltetrazol-5-yl)thio]methyl]-8-oxo-5-thia-1-azabicyclo[4.2.0]-oct-2-ene-2-carboxylic acid |
| 7-amino-3-[[(1,2,3-triazol-5-yl)thio]methyl]-8-oxo-5-thia-1-azabicyclo[4.2.0]oct-2-ene-2-carboxylic acid | α-Carboxy(2,3-dihydro-5-benzofuranyl)acetic acid | 16 | 7-[[carboxy(2,3-dihydro-5-benzofuranyl)acetyl]amino]-3-[[(1,2,3-triazol-5-yl)thio]methyl]-8-oxo-5-thia-1-azabicyclo[4.2.0]oct-2-ene-2-carboxylic acid |
| 7-amino-3-methyl-8-oxo-5-thia-1-azabicyclo[4.2.0]oct-2-ene-2-carboxylic acid | α-Sulfo(2,3-dihydro-5-benzofuranyl)acetic acid | 13 | 7-[[sulfo(2,3-dihydro-5-benzofuranyl)acetyl]amino]-3-methyl-8-oxo-5-thia-1-azabicyclo[4.2.0]oct-2-ene-2-carboxylic acid |
| 7-amino-3-[[(5-methyl-1,3,4-thiadiazol-2-yl)-thio]methyl]-8-oxo-5-thia-1-azabicyclo[4.2.0]oct-2-ene-2-carboxylic acid | α-Sulfo(2,3-dihydro-5-benzofuranyl)acetic acid | 13 | 7-[[sulfo(2,3-dihydro-5-benzofuranyl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid |
| 7-amino-3-[[(1,2,3-triazol-5-yl)thio]methyl]-8-oxo-5-thia-1-azabicyclo[4.2.0]oct-2-ene-2-carboxylic acid | α-Sulfo(2,3-dihydro-5-benzofuranyl)acetic acid | 13 | 7-[[sulfo(2,3-dihydro-5-benzofuranyl)acetyl]amino]-3-[[(1,2,3-triazol-5-yl)thio]methyl]-8-oxo-5-thia-1-azabicyclo[4.2.0]oct-2-ene-2-carboxylic acid |

EXAMPLE 23

7-[[Ethoxysulfonyl(2,3-dihydro-5-benzofuranyl)acetyl]-amino]-3-methyl-8-oxo-5-thia-1-azabicyclo[4.2.0]oct-2-ene-2-carboxylic acid

α-Sulfo(2,3-dihydro-5-benzofuranyl)acetic acid, as prepared in Example 7, (5 mmole) is added to 50 ml of ether and 55 mmole of thionyl chloride and 0.3 ml of dimethylformamide. This mixture is stirred at 20° C. for 50 hours. At the end of this time the ether and the excess thionyl chloride are removed. The dichloride crystallizes after it is cooled overnight. Then 5 mmole of the dichloride is added to 50 ml of anhydrous ether. Then 10 ml of ether containing 5 mmole of water is added and the mixture stirred. The hydrolysis is being complete, The solvent is removed along with the hydrogen chloride liberated. The residue is α-chlorosulfonyl(2,3-dihydro-5-benzofuranyl)acetic acid.

α-Chlorosulfonyl(2,3-dihydro-5-benzofuranyl)acetic acid (5 mmole) is added to 30 ml of ethyl ether. To this mixture is added 5 mmole of ethanol in 10 ml of ethyl ether which contains 10 mmole of triethylamine. The mixture is stirred at 20° C. for about 1 hour and 50 ml of water is added. The pH is adjusted to about 6.5 and the layers separated. The organic layer is dried over magnesium sulfate, filtered and evaporated to give α-ethoxysulfonyl(2,3-dihydro-5-benzofuranyl)acetic acid.

α-Ethoxysulfonyl(2,3-dihydro-5-benzofuranyl acetic acid (5mmole) in 50 ml of dry ether is reacted with about 5.5 mole of thionyl chloride at 20° C. for 4 hours. At the end of this time the solvent is removed to insure that all of the thionyl chloride and hydrochloric acid is removed. The residue is then redissolved in 10 ml of ether. This ether solution is added to 10 ml of water containing 5 mmole of 7-amino-3-methyl-8-oxo-5-thia-1-azabicyclo[4.2.0]oct-2-ene-2-carboxylic acid and 10 mmole of sodium bicarbonate. The temperature of the aqueous solution is about 10° C. After stirring for about 2 hours, the pH is adjusted to about 2. Ethyl acetate is added, the mixture is thoroughly agitated and the layers separated. The organic layer is dried over magnesium sulfate, filtered and evaporated to give the title compound.

In like manner and using the appropriate amount of 3-[(acetyloxy)methyl]-7-amino-8-oxo-5-thia-1-azabicyclo[(4.2.0]oct-2-ene-2-carboxylic acid, tert-butyl ester in place of 7-amino-3-methyl-8-oxo-5-thia-1-azabicyclo[4.2.0]oct-2-ene-2-carboxylic acid gives 3-[(acetyloxy)methyl]-7-[[ethoxysulfonyl(2,3-dihydro-5-benzofuranyl)acetyl]amino-8]-oxo-5-thia-1-azabicyclo[4.2.0]oct-2-ene-2-carboxylic acid tert-butyl ester.

I claim:

1. A compound selected from the formula

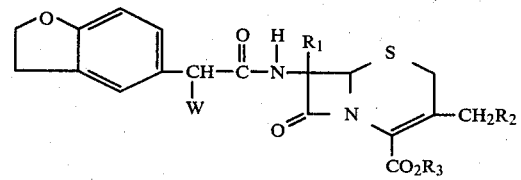

wherein W is selected from the group consisting of H, —NHR$_4$, —OH, —CO$_2$R$_5$ and —SO$_3$R$_5$, wherein R$_4$ is hydrogen, a straight or branched 2 to 5 carbon alkanoyl group or an alkoxycarbonyl group in which the alkoxy moiety is straight or branched and has from 1 to 4 carbon atoms and R$_5$ is hydrogen or a straight or branched alkyl group of from 1 to 4 carbon atoms; R$_1$ is hydrogen or methoxy, R$_2$ is selected from the group consisting of hydrogen, an alkanoyloxy group in which the alkanoyl moiety is straight or branched and has from 2 to 5 carbon atoms and a heterocyclic thio group selected from the group consisting of 1,3,4-thiadiazol-2-ylthio, 5- methyl-1,3,4-thiadiazol-2-ylthio, 1,3,4-oxadiazol-2-ylthio, 5-methyl-1,3,4-oxadiazol-2-ylthio, tetrazol-5-ylthio, 1-methyltetrazol-5-ylthio, 1,2,3-triazol-5-ylthio and 1-methyl-1,2,3-triazol-5-ylthio; $R_3$ is selected from the group consisting of hydrogen, a straight or branched alkyl group of from 1 to 4 carbon atoms, an alkanoyloxymethyl group in which the alkanoyl moiety is straight or branched and has from 2 to 5 carbon atoms, an alkanoylaminomethyl group wherein the alkanoyl moiety is straight or branched and has from 2 to 5 carbon atoms and the amino nitrogen is substituted with hydrogen or a straight or branched alkyl group of from 1 to 4 carbon atoms, an alkoxycarbonylaminomethyl group wherein the alkoxy moiety is straight or branched and has from 1 to 4 carbon atoms and the amino nitrogen is substituted with hydrogen or a straight or branched alkyl group of from 1 to 4 carbon atoms, a p-(alkanoyloxy)benzyl group in which the alkanoyl moiety has from 2 to 5 carbon atoms and is straight or branched, and an aminoalkanoyloxymethyl group wherein the alkanoyl moiety is straight or branched and has from 2 to 15 carbon atoms and the amino nitrogen is hydrogen, mono- or di-substituted with a straight or branched alkyl group of from 1 to 4 carbon atoms; and non-toxic pharmaceutically acceptable salts and individual optical isomers thereof.

2. A compound of claim 1 in which $R_1$ and $R_3$ are both hydrogen.

3. A compound of claim 2 in which $R_2$ is hydrogen, acetyloxy, 1,2,3-triazol-5-ylthio, 5-methyl-1,3,4-thiadiazol-2-ylthio, 1,3,4-thiadiazol-2-ylthio, tetrazol-5-ylthio and 1-methyltetrazol-5-ylthio.

4. A compound of claim 1 which is 7-[[α-amino(2,3-dihydro-5-benzofuranyl)acetyl]amino]-3-methyl-8-oxo-5-thia-1-azabicyclo[4.2.0]oct-2-ene-2-carboxylic acid or a pharmaceutically acceptable salt thereof.

5. A compound of claim 1 which is 7-[[D-α-amino(2,3-dihydro-5-benzofuranyl)acetyl]amino]-3-methyl-8-oxo-5-thia-1-azabicyclo[4.2.0]oct-2-ene-2-carboxylic acid or a pharmaceutically acceptable salt thereof.

6. A compound of claim 1 which is 7-[[(2,3-dihydro-5-benzofuranyl)hydroxyacetyl]amino]-3-methyl-8-oxo-5-thia-1-azabicyclo[4.2.0]oct-2-ene-2-carboxylic acid or a pharmaceutically acceptable salt thereof.

7. A compound of claim 1 which is 3-[(acetyloxy)methyl]-7-[[D-α-amino(2,3-dihydro-5-benzofuranyl)acetyl]amino]-8-oxo-5-thia-1-azabicyclo[4.2.0]oct-2-ene-2-carboxylic acid or a pharmaceutically acceptable salt thereof.

8. A compound of claim 1 which is 3-[(acetyloxy)methyl]-7-[[(2,3-dihydro-5-benzofuranyl)hydroxyacetyl]amino]-8-oxo-5-thia-1-azabicyclo[4.2.0]oct-2-ene-2-carboxylic acid or a pharmaceutically acceptable salt thereof.

9. A compound of claim 1 which is 7-[[D-α-amino(2,3-dihydro-5-benzofuranyl)acetyl]amino]-3-[[(1,2,3-triazol-5-yl)thio]methyl]-8-oxo-5-thia-1-azabicyclo[4.2.0]oct-2-ene-2-carboxylic acid or a pharmaceutically acceptable salt thereof.

10. A compound of claim 1 which is 7-[[D-α-amino(2,3-dihydro-5-benzofuranyl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid or a pharmaceutically acceptable salt thereof.

11. A compound of claim 1 which is 7-[[α-amino(2,3-dihydro-5-benzofuranyl)acetyl]amino]-3-[[(1-methyltetrazol-5-yl)thio]methyl]-8-oxo-5-thia-1-azabicyclo[4.2.0]oct-2-ene-2-carboxylic acid or a pharmaceutically acceptable salt thereof.

* * * * *